US007041139B2

(12) United States Patent
Bluni et al.

(10) Patent No.: US 7,041,139 B2
(45) Date of Patent: May 9, 2006

(54) URETERAL STENTS AND RELATED METHODS

(75) Inventors: Scott Bluni, Sudbury, MA (US); Barry Gellman, North Easton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/014,678

(22) Filed: Dec. 11, 2001

(65) Prior Publication Data
US 2003/0109930 A1    Jun. 12, 2003

(51) Int. Cl.
*A61F 2/36* (2006.01)
(52) U.S. Cl. .................. 623/23.66; 623/23.64
(58) Field of Classification Search ............... 623/23.7; 128/898
See application file for complete search history.

(56) References Cited

U.S. PATENT DOCUMENTS

| 3,890,977 | A |   | 6/1975  | Wilson .................... 128/418 |
|-----------|---|---|---------|------------------------------------|
| 4,212,304 | A |   | 7/1980  | Finney .................... 128/349 |
| 4,307,723 | A |   | 12/1981 | Finney .................... 128/349 |
| 4,334,327 | A |   | 6/1982  | Lyman et al. .................. 3/1 |
| 4,416,267 | A | * | 11/1983 | Garren et al. .................. 128/1 |
| 4,531,933 | A |   | 7/1985  | Norton et al. .................. 604/8 |
| 4,568,338 | A |   | 2/1986  | Todd .................... 604/281 |
| 4,580,568 | A |   | 4/1986  | Gianturco .................. 128/345 |
| 4,610,657 | A |   | 9/1986  | Densow .................... 604/8 |
| 4,643,716 | A |   | 2/1987  | Drach .................... 604/8 |
| 4,671,795 | A |   | 6/1987  | Mulchin .................... 604/281 |
| 4,713,049 | A |   | 12/1987 | Carter .................... 604/8 |
| 4,738,667 | A |   | 4/1988  | Galloway .................. 604/281 |
| 4,762,128 | A |   | 8/1988  | Rosenbluth ................ 128/343 |
| 4,787,884 | A |   | 11/1988 | Goldberg .................... 604/8 |
| 4,790,810 | A |   | 12/1988 | Pugh, Jr. et al. ............ 604/8 |
| 4,813,925 | A |   | 3/1989  | Anderson, Jr. et al. ........ 604/8 |
| 4,820,262 | A |   | 4/1989  | Finney .................... 604/8 |
| 4,846,814 | A |   | 7/1989  | Ruiz .................... 604/281 |
| 4,874,360 | A |   | 10/1989 | Goldberg et al. ............ 604/8 |
| 4,887,996 | A |   | 12/1989 | Bengmark .................. 604/54 |
| 4,931,037 | A |   | 6/1990  | Wetterman .................. 604/8 |
| 4,950,228 | A |   | 8/1990  | Knapp, Jr. et al. .......... 604/8 |
| 4,990,133 | A |   | 2/1991  | Solazzo .................... 604/8 |
| 5,052,998 | A |   | 10/1991 | Zimmon .................... 604/8 |
| 5,078,736 | A |   | 1/1992  | Behl .................... 623/1 |
| 5,116,309 | A |   | 5/1992  | Coll .................... 604/8 |
| 5,141,502 | A |   | 8/1992  | Macaluso, Jr. ............ 604/281 |
| 5,176,625 | A |   | 1/1993  | Brisson .................... 604/8 |
| 5,176,626 | A |   | 1/1993  | Soehendra .................. 604/8 |
| 5,221,253 | A |   | 6/1993  | Coll .................... 604/8 |
| 5,224,953 | A |   | 7/1993  | Morgentaler ................ 606/192 |

(Continued)

FOREIGN PATENT DOCUMENTS

EP        1062920       12/2000

(Continued)

OTHER PUBLICATIONS

"Specific gravity of major polymers", 1999, http://www.plasticsusa.com/specgrav.html.*
Hepperlen, T., et al., *Self-Retained Internal Ureteral Stents :A New Approach*, The Journal of Urology, vol. 119 (1978), pp. 731-734.

(Continued)

*Primary Examiner*—Thomas Barrett

(57) ABSTRACT

A medical device for use within a body cavity comprising an elongated body portion and a retention module. The retention module comprises a fixation element and a tether connector. The tether connector and fixation element permit the device to move a predetermined distance longitudinally. The tether connector reduces ureteral reflux, and minimizes irritation and patient discomfort. The fixation element and the tether connector further function as a graspable structure for removal of the stent.

30 Claims, 4 Drawing Sheets

U.S. PATENT DOCUMENTS

| | | | |
|---|---|---|---|
| 5,234,456 A | 8/1993 | Silvestrini | 606/194 |
| 5,269,802 A | 12/1993 | Garber | 606/191 |
| 5,282,784 A | 2/1994 | Willard | 604/8 |
| 5,346,467 A | 9/1994 | Coll | 604/8 |
| 5,354,263 A | 10/1994 | Coll | 604/8 |
| 5,364,340 A | 11/1994 | Coll | 604/8 |
| 5,380,270 A | 1/1995 | Ahmadzadeh | 604/9 |
| 5,401,257 A | 3/1995 | Chevalier, Jr. et al. | 604/265 |
| 5,507,769 A | 4/1996 | Marin et al. | 606/198 |
| 5,514,176 A | 5/1996 | Bosley, Jr. | 623/1 |
| 5,520,697 A | 5/1996 | Lindenberg et al. | 606/108 |
| 5,531,741 A | 7/1996 | Barbacci | 606/15 |
| 5,599,291 A | 2/1997 | Balbierz et al. | 604/8 |
| 5,647,843 A | 7/1997 | Mesrobian et al. | 604/8 |
| 5,662,713 A | 9/1997 | Andersen et al. | 623/12 |
| 5,681,274 A | 10/1997 | Perkins et al. | 604/8 |
| 5,683,448 A | 11/1997 | Cragg | 623/1 |
| 5,709,874 A | 1/1998 | Hanson et al. | 424/423 |
| 5,716,393 A | 2/1998 | Lindenberg et al. | 623/1 |
| 5,755,722 A | 5/1998 | Barry et al. | 606/108 |
| 5,766,209 A | 6/1998 | Devorec | 604/8 |
| RE35,849 E | 7/1998 | Soehendra | 604/8 |
| 5,795,319 A | 8/1998 | Ali | 604/8 |
| RE35,988 E | 12/1998 | Winston et al. | 623/1 |
| 5,928,280 A | 7/1999 | Hansen et al. | 623/1 |
| 5,964,744 A | 10/1999 | Balbierz et al. | 604/530 |
| 5,968,088 A | 10/1999 | Hansen et al. | 623/1 |
| 5,971,967 A | 10/1999 | Willard | 604/264 |
| 6,013,854 A | 1/2000 | Moriuchi | 623/11 |
| 6,110,212 A | 8/2000 | Gregory | 623/23.72 |
| 6,176,875 B1 | 1/2001 | Lenker et al. | 623/1.49 |
| 6,258,098 B1 * | 7/2001 | Taylor et al. | 606/108 |
| 2002/0173754 A1 * | 11/2002 | Whitmore, III | 604/264 |

FOREIGN PATENT DOCUMENTS

| | | | |
|---|---|---|---|
| WO | WO 99/24106 | * | 5/1999 |
| WO | 99/58083 | | 11/1999 |
| WO | WO 99/58083 | * | 11/1999 |
| WO | 00/51521 | | 9/2000 |
| WO | 00/66032 | | 9/2000 |
| WO | WO 00/66032 | * | 11/2000 |
| WO | WO 01/091668 A1 | * | 12/2001 |

OTHER PUBLICATIONS

Camacho, M. F., et al., *Double-Ended Pigtail Ureteral Stent: Useful Modification to Single End Ureteral Stent*, Urology, vol. 13, No. 5 (May 1979), pp. 516-520.

Mardis, H. K., et al., *Double Pigtail Ureteral Stent*, Urology, vol. 14, No. 1, (Jul. 1979), pp. 23-26.

Mardis, H. K., et al., *Polyethylene Double-Pigtail Ureteral Stents*, Urologic Clinics of North America, vol. 9, No. 1 (Feb. 1982), pp. 95-101.

Stables, D., *Percutaneous Nephrostomy: Techniques, Indications, and Results*, Urologic Clinics of North America, vol. 9, No. 1, (Feb. 1982), pp. 15-29.

Minkov, N., et al., *Our Experience in the Application of the Biocompatible Indwelling Ureteral Stents*, International Urology and Nephrology, vol. 18, No. 4 (1986), pp. 403-409.

Mardis, H. K., *Evaluation of Polymeric Materials for Endourologic Devices*, Seminars in Interventional Radiology, vol. 4, No. 1, (Mar. 1987), pp. 36-45.

Birch, B.R.P. et al., *Tethered Ureteric-Stents—A Clinical Assessment*, Bristish Journal of Urology, vol. 62 (1988), pp. 409-411.

Mardis, H. K., et al., *Ureteral Stents*, Urologic Clinics of North America, vol. 15, No. 3 (1988), pp. 471-479.

Bard Urological Division—Product Catalog (1990).

Cook Urological—Urological Surgical Products (1990), pp. 176-228.

Mardis, H. K., et al., *Ureteral Stents: Use and Complications*, Problems in Urology, vol. 6, No. 2 (Jun. 1992), pp. 296-306.

Mardis, H. K., et al., *Comparative Evaluation of Materials Used for Internal Ureteral Stent*, Journal of Endourology, vol. 7, No. 2 (1993), pp. 105-115.

Culkin, D. J., *Complications of Ureteral Stents*, Infections in Urology (Sep. 1996), pp. 139-143.

Mardis, H. K., *Self-Retained Internal Ureteral Stents: Use and Complications*, AUA Update Series, Lesson 29, vol. 16 (1997), pp. 226-232.

International Search Report for International Patent Application No. PCT/US02/32115, dated Jan. 7, 2003, 5 pages.

* cited by examiner

URETERAL STENTS AND RELATED METHODS

TECHNICAL FIELD

This invention generally relates to stents and more particularly to ureteral stents.

BACKGROUND INFORMATION

Ureteral stents are used to create a pathway for urinary drainage from the kidney to the bladder in patients with ureteral obstruction or injury or to protect the integrity of the ureter in a variety of surgical manipulations. A number of clinical conditions can produce interruption in urine flow including, for example, intrinsic obstruction of the ureter due to tumor growth, stricture or stones, compression of the ureter due to extrinsic tumor growth, stone fragment impactation in the ureter following extracorporeal shock wave lithotripsy (ESWL), and ureteral procedures such as ureteroscopy and endopyelotomy. Stents may be used to treat or avoid obstructions of the ureter (such as ureteral stones or ureteral tumors) that disrupt the flow of urine from the corresponding kidney to the urinary bladder. Serious obstructions of the urinary tract may cause urine to back up into the kidney, threatening renal function. Ureteral stents may also be used after endoscopic inspection of the ureter.

Ureteral stents typically are tubular in shape, terminating in two opposing ends: a kidney distal end and a urinary bladder proximal end. One or both of the ends of the stent may be coiled in a pigtail spiral or J-shape to prevent the upward and/or downward migration of the stent in the lumen of the ureter due, to day-to-day physical activity of the patient, for example. A kidney end coil is designed to retain the stent within the renal pelvis and to prevent stent migration down the ureter. The urinary bladder end coil is positioned in the bladder and is designed to prevent stent migration upward toward the kidney. The bladder end-coil is also used to aid in retrieval and removal of the stent.

A ureteral stent assists in the flow of urine from the kidney to the urinary bladder. The region known as the ureteral vesical junction is a small area of the ureter that is immediately upstream, relative to normal urine flow, to the urinary bladder. The ureteral vesical junction has greater pain sensation relative to other regions of the ureter wall and kidneys and is a major source of patient discomfort when this region of the ureter is in contact with indwelling ureteral stents.

Ureteral stents, particularly the portion positioned in the ureter and proximal to the bladder, may produce adverse effects including hemorrhage, a continual urge to urinate, flank pain accompanying reflux of urine back up the ureter due to retrograde pressure when voiding, and trigone irritation resulting from chronic irritation due to the bladder anchoring features of the stent or resulting from intraoperative trauma inflicted from passage of the device in the ureter. In summary, stents may cause or contribute to significant patient discomfort and serious medical problems.

SUMMARY OF THE INVENTION

In general, one aspect of the invention described herein relates to a medical device for use within a body tract such as a duct, tube or vessel. In one embodiment of this aspect of the invention, the medical device has an elongated body portion defining a lumen and a proximal portion with a proximal end, a distal portion with a distal end, and a retention module disposed proximal to the proximal end of the elongated body portion. The retention module retains the proximal end of the body portion of the stent in the ureter just distal to the urinary bladder. The retention module further includes a fixation element attached to the elongated body portion by a tether connector. The tether connector reduces ureteral reflux and patient discomfort by permitting the ureteral orifice to contract more completely around the tether connector during voiding (urination) than is possible around the elongated body portion of the stent. The tether connector or the fixation element of the retention module may also be a suitable structure for grasping and removal of the stent from the body.

In another embodiment, the fixation element of the retention module is substantially buoyant. In this embodiment, the buoyant fixation element may float on the urine within the bladder thereby minimizing contact of the fixation element with the tri gone of the bladder. In some embodiments, the fixation element of the retention module is of a size and configuration so as to prohibit the passage of said fixation element from the lumen of the urinary bladder into the lumen of the ureter and to allow the endoscopic introduction of the fixation element into the urinary bladder.

In other embodiments, the fixation element may be a planar spiral, a substantially helical spiral, or substantially spherical. In the substantially spherical form, the fixation element may have a diameter greater than the diameter of the lumen of the ureter. In another embodiment, the proximal portion of the elongated body portion is substantially more compressible than remaining portions of the elongated body portion. In this embodiment, the proximal portion of the elongated body portion will collapse with pressure exerted on it by adjacent body tissue, by peristaltic motion, or by sphincter contraction, for example.

In further embodiments, the retention module may have multiple tether connectors and/or multiple fixation elements to facilitate urinary drainage during conditions of peri-renal or peri-ureteral edema, for example. The tether connector of the retention module may be substantially elastic to provide a strain relief function and to minimize longitudinal movement of the stent in the ureter in the direction of the kidney when there is movement of the kidney relative to the bladder, such as during normal respiration. In different embodiments, the tether connector may be substantially rigid. In other embodiments, the elongated body portion may be substantially rigid to prevent deformation during the insertion of the device through the ureter. In another embodiment, the elongated body portion may define a plurality of openings along its length to further facilitate fluidic communication between the lumen of the body portion and the body tract where the body portion is disposed.

A second aspect of the invention describes a method of treating at least partial ureteral obstruction of a patient. The method according to the invention includes the steps of providing a medical device with an elongated body portion defining a lumen and having a proximal end, a distal end, a proximal portion, a distal portion, a retention module attached to the proximal end of the elongated body portion by a tether connector, and inserting the medical device into the patient such that the fixation element is positioned in the bladder of the patient.

The foregoing and other objects, features and advantages of the present invention disclosed herein, as well as the invention itself, will be more fully understood from the following description of preferred embodiments and claims, when read together with the accompanying drawings. In the drawings, like reference characters generally refer to the same parts throughout the different views. The drawings are not necessarily to scale, emphasis instead generally being placed upon illustrating the principles of the invention.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

This invention generally concerns a drainage device that, when positioned within a body tract such as a duct, tube, or vessel of a mammal, assists in reducing fluid retention with minimal patient discomfort. For simplicity and for illustrative purposes, the invention is described here in the context of draining urine from the urinary tract such as a kidney, through a ureter, and into the urinary bladder. However, the invention is applicable to any situation that requires drainage of fluid from any site within the body. Application of the invention also applies to body sites in the body other than the urinary tract such as, for example, drainage from the gall bladder, or other biliary structures, to the duodenum.

Figures 1A, 1B:
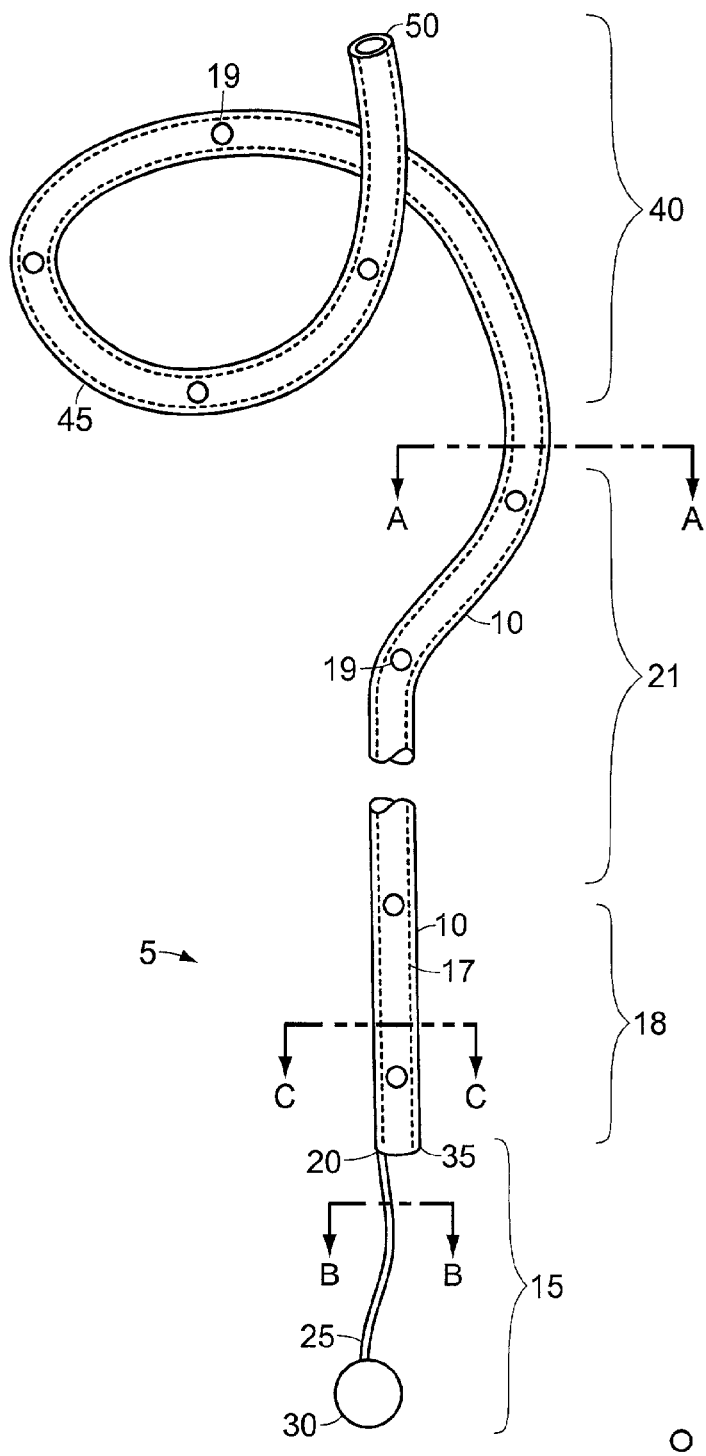
FIG. 1A is a plan view of a ureteral stent according to one embodiment of the invention.
FIG. 1B is a cross-sectional view of the ureteral stent illustrated in FIG. 1A, taken along the line B—B.

Referring to FIG. 1A, in general, a medical device according to the invention, for example, a stent 5, is illustrated. The stent 5 includes an elongated tubular body portion 10, a retention module 15, a mid-portion 21, a proximal portion 18 terminating in a proximal drainage end 35, and a distal portion 40 terminating in a distal drainage end 50. The retention module 15 is attached to the proximal drainage end 35 at an attachment site 20 and includes a fixation element 30 and a tether connector 25.

Typically, in a ureteral application, the length of the elongated body portion 10 ranges between about 18 cm to 30 cm, preferably about 18 cm to 20 cm. In one embodiment, the body portion 10 of the ureteral stent 5 includes at least one lumen, such as lumen 12 illustrated, for example, in FIG. 1D. The elongated body portion 10 has an outside diameter of at least about 1.6 mm to 3.3 mm, preferably 2 mm (or French size 6). The thickness of a wall 17 of the elongated body portion 10 is at least about 0.05 mm to 0.35 mm, preferably about 0.2 mm. The stent 5 may be constructed from biocompatible plastics or polymers including polytetrafluoroethylene (PTFE), silicone polyurethane, polyurethane plastics, polyethylene plastics, and thermoplastics, for example.

With continued reference to FIG. 1A, in one embodiment according to the invention, the elongated body portion 10 of the stent 5 has one or more openings 19 which may be, for example, holes, pores, slits, or apertures, through the wall 17 of the stent 5. The openings 19 allow fluidic communication between the outer surface of the stent 5 with the lumen 12 defined by the wall 17 of the ureter, for example. The elongated body portion 10 has a cross-sectional area as shown in, for example, FIG. 1D.

Figure 1C:
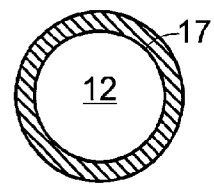
FIG. 1C is a cross-sectional view of the ureteral stent illustrated in FIG. 1A, taken along the line C—C
Figure 1D:
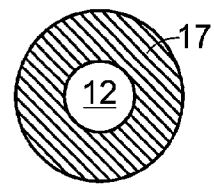
FIG. 1D is a cross-sectional view of the ureteral stent illustrated in FIG. 1A, taken along the line A—A.
Figure 1E:
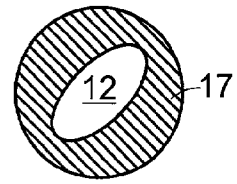
FIG. 1E illustrates the ureteral stent with a lumen having an oval cross-section according to one embodiment of the invention.
Figure 1F:
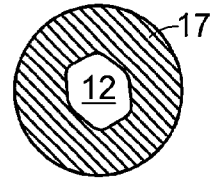
FIG. 1F illustrates the ureteral stent with a lumen having a polygonal cross-section according to one embodiment of the invention.
Figure 1G:
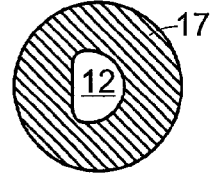
FIG. 1G illustrates the ureteral stent with a lumen having a D-shaped cross-section according to one embodiment of the invention.
Figure 1H:
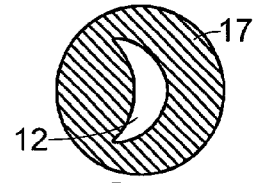
FIG. 1H illustrates the ureteral stent with a lumen having a crescent-shaped cross-section according to one embodiment of the invention.
Figure 1I:
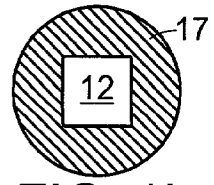
FIG. 1I illustrates the ureteral stent with a lumen having a rectangular cross-section according to one embodiment of the invention.

In one embodiment according to the invention illustrated in FIG. 1C, the wall thickness at the proximal portion 18 of the elongated body portion 10 of stent 5 is reduced, i.e., thinner relative to the thickness of the wall 17 of the other portions of the elongated body portion 10, for example, the mid-portion 21 illustrated in FIG. 1D. The wall 17 is thinner in the proximal portion 18 for the purpose of making the proximal portion 18 more compressible or collapsible relative to at least the mid portion 21 of the elongated body portion 10. The collapsible wall 17 is compressible such that the wall 17 of the stent 5 in the proximal portion 18 will collapse with pressure exerted on it by adjacent body tissue, by peristaltic motion, or by sphincter contraction, for example. The collapsible wall 17 in the proximal portion 18 is constructed from one or more biocompatible plastics or polymers including, for example, polytetrafluoroethylene (PTFE), silicone, polyurethane, polyurethane plastics, polyethylene plastics, and thermoplastics and it has a thickness of less than 0.07 mm.

Figure 2:
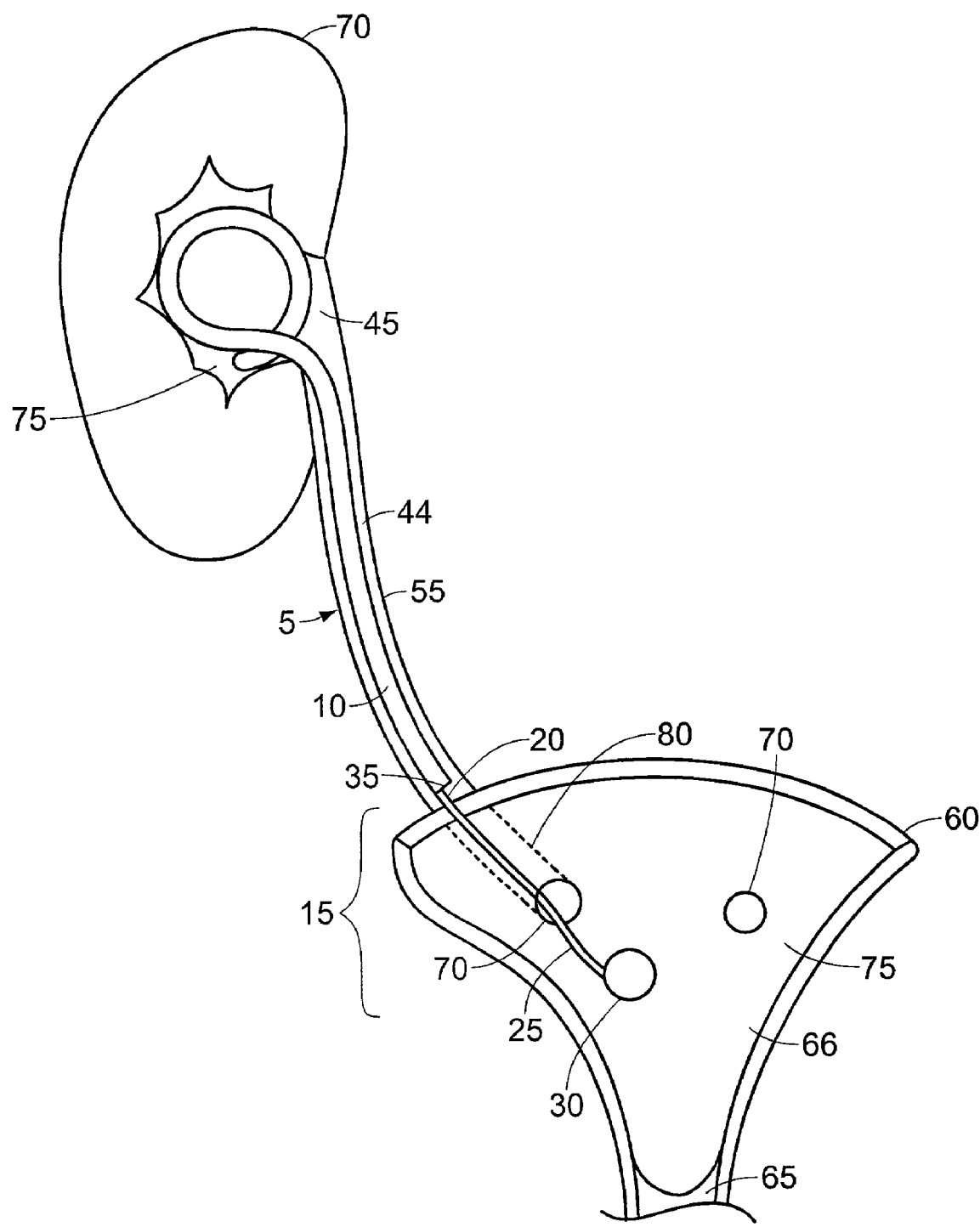
FIG. 2 illustrates a clinical application of a ureteral stent according to the invention.

Referring to FIG. 2, when the proximal portion 18 of the stent 5 is compressible or collapsible, chafing and irritation of the ureter 55 is less than with more rigid stents, thereby increasing the comfort level of the patient. By employing a thinner wall 17 in the proximal portion 18 than in the other portions of the elongated body portion 10, normal drainage of urine through the stent 5 is facilitated while some resistance to retrograde reflux of urine toward the kidney is maintained. Alternatively, the wall 17 of the stent 5 may be sized and configured with a length sufficient to extend the whole length of the ureter 55 from the renal pelvis 95 through and into the urinary bladder 60.

The wall 17 in the distal region 40 of the elongated body portion 10, for example, as illustrated in FIG. 1D. is sufficiently thick to be generally resistant to deformation and crimping. Patency of the ureter 55 is maintained when the stent 5 is placed in the ureter 55 even when the ureter might otherwise be constricted due to enlargement of tissue surrounding the stent 5 or movement of the ureter 55 due to patient movement or peristaltic motions. The wall 17 of the distal region 40 of the elongated body portion 10, resists collapsing upon radial or lateral pressure by the surrounding body tissue or by longitudinal pressure exerted on the wall 17 during insertion of the stent 5 into the body cavity. These properties resisting crimping are imparted to the stent 5 by varying the thickness of the wall 17 of the stent 5 relative to the rigidity of the material used to manufacture the stent 5. For example, a wall thickness of 0.05 to 0.35 mm may be used with materials such as silicone, polytetrafluoroethylene (PTFE), polyurethane plastics, and polyethylene plastics. Referring to FIGS. 1D–1I, for example, the cross-section of the lumen 12 of stent 5, may be any shape that allows the flow of liquid through the lumen 12 including round, oblong, elliptical, hexagonal, D-shaped, crescent-shaped and rectangular, for example.

As shown in FIG. 2, the elongated tubular body portion 10 of the stent 5 extends from the renal pelvis 95 of the kidney 90 in the lumen 44 of the ureter 55 to a terminus at the proximal drainage end 35 positioned upstream of the urinary bladder 60.

Figure 3A:
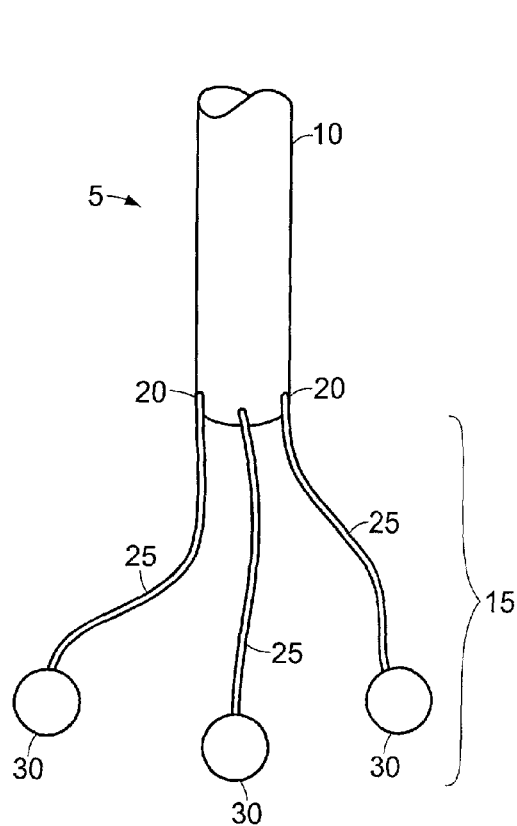
FIGS. 3A–3C illustrate enlarged views of embodiments of the retention module of proximal portion of the stent according to the invention.
Figure 3C:
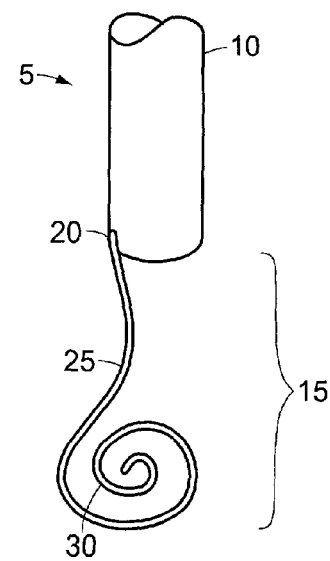
Figure 3B:
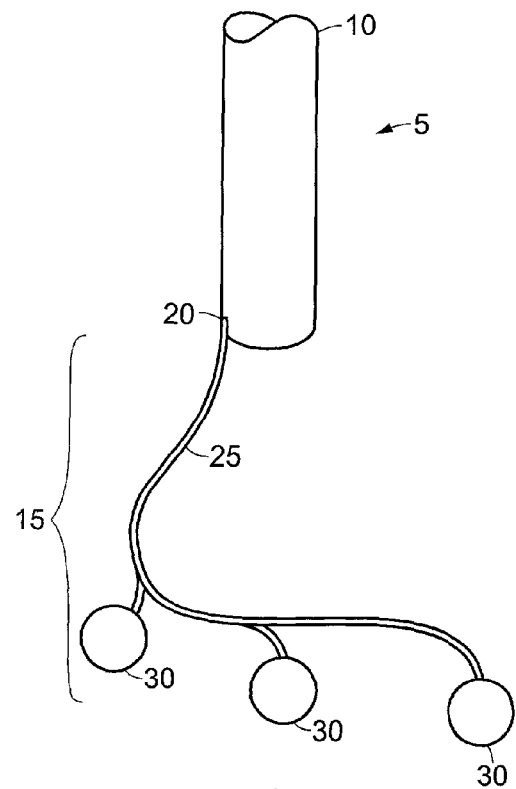

The retention module 15, illustrated in FIGS. 3A–3C, extends from the proximal drainage end 35 of stent 5 through the intramural tunnel 80 of the urinary bladder 60 and through ureteral orifice 70 where the retention module 15 ends in the lumen 66 of the urinary bladder 60.

Referring to FIG. 3A, the retention module 15 includes at least one fixation element 30 and one or more tether connectors 25. In one embodiment, illustrated in FIGS. 3A and 3B, the fixation element 30 is a substantially spherical bead having an outside diameter in the range of 3 to 10 mm, preferably 5 mm. In other embodiments, fixation element 30 may include a variety of other shapes, for example an oval, tear-shaped, or peanut-shaped bead. In one particular embodiment, illustrated in FIG. 3C, the fixation element 30 of the retention module 15 is a suitable anchor such as, for example, a pigtail shape. Fixation element 30 is not limited to the foregoing and can be any shape that limits the passage of the fixation element 30 through the ureteral orifice 70.

According to one embodiment of the invention, the fixation element 30 of the retention module is manufactured from a polymer that permits fixation element 30 to remain buoyant. Some copolymers that may be used to manufacture fixation elements 30 include, for example, a copolymer such as PERCOFLUX® (Medi-Tech, Inc.), C-FLEX® (Xomed-Trease, Inc.), FLEXIMA™, or a high density polyethylene or PTFE such as TEFLON® (E.I. Du Pont De Nemours and Company, Inc.) that permit fixation element 30 to remain buoyant. In a particular embodiment according to the invention, the fixation element 30 is buoyant relative to the specific gravity of the medium, such as urine, in which the fixation element 30 is suspended. This characteristic permits at least the fixation element 30 of the retention module 15 to remain buoyant in the lumen 66 of the urinary bladder 60 illustrated in FIG. 2. Alternatively, the fixation element 30 of retention module 15 is hollow and contains air, another gas, or a substance that adds buoyancy. The buoyancy of the fixation element 30 prevents the fixation element 30 from contacting and irritating the trigone 75 of the urinary bladder 60, illustrated in FIG. 2, thereby minimizing patient discomfort.

Referring again to FIG. 1A, retention module 15 is attached to elongated body portion 10 of stent 5 at attachment site 20 at the proximal drainage end 35 of stent 5. The tether connector 25 of the retention module 15 has a total length in the range of about 2 to 5 cm, preferably 3 cm, a diameter in the range of about 0.15 to 0.23 mm, preferably 0.2 mm. In one embodiment, the tether connector 25 is made of an elastomeric material, for example, HYTREL® (E.I. Du Pont De Nemours and Company, Inc.), silicone, or a thermoplastic elastomer (TPE), to provide strain relief. Typically the tether connector 25 as illustrated in FIG. 1B, is cord-like, lacking a lumen. In different embodiments, the tether connector 25 may be substantially elastic and flexible or the tether connector 25 maybe substantially rigid and inflexible.

Referring again to FIG. 3A, the tether connector 25 may be integral with, or detachable from, the elongated body portion 10. For example, tether connector 25 may be integrally formed as part of the proximal portion 18 of the body portion 10, the circumference of which is subsequently and substantially removed through an appropriate manufacturing process to yield tether connector 25. Alternatively, tether connector 25 is attached at attachment site 20 of stent 5 before replacement of the stent 5 in the body cavity. In the latter example, tether connector 25 is reversibly attached to elongated body portion 10 at attachment site 20 by any suitable means, such as, for example, by adhesive, or by mechanical connection. Suitable mechanical connections include, for example, threading and tying tether connector 25 through an opening (not shown) in the wall 17 of body portion 10, or forming tether connector 25 with a preformed shape such as a hook that connects with an opening or attachment site 20 associated with elongated body portion 10.

Referring again to FIG. 2, after the stent 5 is deployed in the body, the tether connector 25 is located within the intramural tunnel 80 of the urinary bladder 60. In general, the length of the tether connector 25 is in the range of about 2 to 5 cm, preferably 3 cm. In one embodiment, the ends of the tether connector 25 extend proximal and distal to the intramural tunnel 80. The tether connector 25 allows for anatomical variation among patients by compensating for variations in length of the intramural tunnel 80 from patient to patient. The fixation element 30 and/or the tether connector 25 may be grasped by an operator for easy removal of the stent 5 from its location in the body. The tether connector 25 and fixation element 30 of the retention module 15 permit the stent 5 to freely migrate longitudinally in the lumen 44 of the ureter 55 by a distance determined by the length of the tether connector 25. By flexibly, yet securely joining the proximal portion 18 of the stent 5 to the fixation element 30 by means of a tether connector 25, the tether connector 25 provides resistance to upward movement of stent 5 in the direction of the kidney 90 during movement of the kidneys caused by respiration, peristalsis or other voluntary or involuntary activity of the patient. The migration of the stent 5 by a fixed distance that corresponds to the length of the tether connector 25 minimizes the irritation and patient discomfort that can be caused by conventional stent anchoring elements that substantially fix the stent 5 in one position in the ureter 55 and do not permit the stent 5 to migrate with body movements.

The tether connector 25, according to the invention, extends from the proximal end 35 of the stent 5 and has a smaller diameter than the elongated body portion 10. Because of its small diameter, tether connector 25 minimizes ureteral reflux, (i.e., flow of urine back up the ureter toward the kidney during voiding) because the intramural tunnel 80 of the urinary bladder 60 is collapsed around the small diameter tether connector 25 when the urinary bladder contracts during voiding. Tether connector 25 also minimizes patient discomfort associated with obstructions in the ureteral orifice 70. The number, size and configuration of fixation elements 30, as described below, may be customized to accommodate the migration-prevention requirements of the particular stent to be implanted in the patient's body.

In another embodiment of the invention illustrated in FIG. 3A, the retention module 15 includes a plurality of tether connectors 25 attached to the attachment site 20 of the elongated body portion 10. The plurality of tether connectors 25 facilitates urinary drainage through the intramural tunnel 80 of the urinary bladder 60, shown in FIG. 2 under numerous pathological conditions including, for example, swelling of the tissue in and around intramural tunnel 80 caused by edema induced by trauma during insertion of the stent 5. The combined action of the plurality of tether connectors 25 permits wicking of urine to the urinary bladder 60 but reduces urine reflux from the urinary bladder 60 retrograde to the ureter 55. In this embodiment, at least one tether connector 25 is attached to the fixation element 30. In another embodiment, illustrated, for example, in FIG. 3B, more than one multiple fixation element 30 may be attached to each of the tether connectors 25.

Figure 4A:
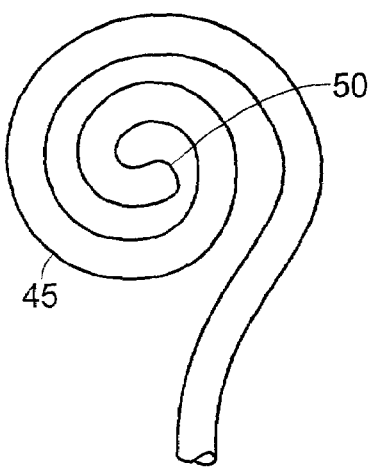
FIGS. 4A–4C illustrate various embodiments of the distal portion of the stent according to the invention.
Figure 4B:
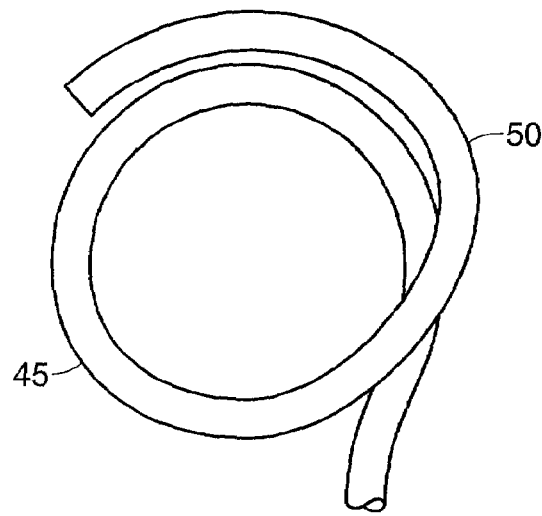
Figure 4C:
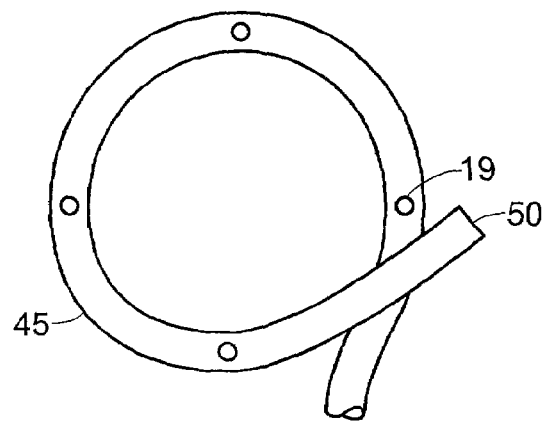

FIGS. 4A–4C depict an enlarged view of the various embodiments of distal portion 40. The stent 5 includes a kidney retention anchor or pigtail 45 at the distal portion 40. The pigtail 45 is formed by bending the distal portion 40 of the stent 5 into a planar or substantially planar spiral. The pigtail 45 is shown having one of a variety of possible configurations that serve to retain the stent 5 in the renal pelvis 95 of the kidney 90. In one embodiment, as shown in FIG. 4A, the pigtail 45 is formed by shaping the distal portion 40 of the stent 5 into a spiral planar coil formed with a multiplicity of turns wound concentrically within the same plane. In another embodiment, as shown in FIG. 4B, the pigtail 45 is formed by shaping the distal portion 40 of the stent 5 into a helical coil formed with at least one wound turn. In a further embodiment, as shown in FIG. 4C, the pigtail 45 is formed at the distal portion 40 of the stent 5 with at least one helical coil further comprises a plurality of openings 19 arranged in various patterns.

Referring again to FIG. 2, according to another embodiment of the invention, stent 5 is deployed by an operator in the ureter 55, by inserting a relatively rigid wire guide (not shown) into lumen 12 of the stent 5 from the proximal portion 18 of the stent 5 to the distal portion 40 of the stent 5. If the stent 5 includes a pigtail 45 at the distal portion 40 of the elongated portion 10, the wire guide straightens out the spiral pigtail 45 prior to insertion of the stent 5 into the patient's body. The wire guide, together with the stent 5, is inserted by an operator either endoscopically or transurethrally into the urinary bladder 60. The stent 5 is advanced through one of the ureteral orifices 70 and along the lumen 44 of the ureter 55 via a pushing action until the distal portion 40 of the stent 5 is proximal to the renal pelvis 95. The wire guide is then withdrawn from the lumen 12 of the distal portion 40 of the stent 5 either endoscopically or transurethrally wherein the pigtail 45 returns to its former spiral shape within the renal pelvis 95. The spiral shape of pigtail 45 anchors the distal portion 40 thereby reducing longitudinal migration of the stent 5 away from the kidney 90 in the lumen 44 of the ureter 55.

With the distal portion 40 of the stent 5 in place, the wire guide is withdrawn further from the lumen 12 of the elongated body portion 10 of the stent 5 followed by complete removal of the wire guide from the patient. The retention module 15 remains attached to the proximal drainage end 35 of the body portion 10 via the tether connector 25 at the attachment site 20. The tether connector 25 extends through the intramural tunnel 80 to the fixation element 30 and terminates in the lumen 66 of the urinary bladder 60. The stent 5 and the retention module 15 are selected according to the clinical needs of the patient and must be attached to the proximal portion 18 of stent 5 before the insertion of stent 5 into a body cavity.

Variations, modifications, and other implementations of what is described herein will occur to those of ordinary skill in the art without departing from the spirit and the scope of the invention as claimed. Accordingly, the invention is not to be limited to the preceding illustrative description but instead by the spirit and scope of the following claims.

What is claimed is:

1. A ureteral stent for placement in a ureter comprising:
an elongated body portion defining a lumen, said body portion comprising a proximal end for placement within one of a ureter and a bladder of a patient, a distal end for placement within a kidney of the patient, a proximal portion, and a distal portion; and
a retention module disposed proximal to said proximal end of said elongated body portion for retaining a portion of the stent in the bladder, said retention module comprising at least one bead having a diameter between 3 and 10 millimeters, the at least one bead being attached to the elongated body portion by at least one tether connector, wherein the at least one bead is substantially buoyant relative to urine.

2. The ureteral stent of claim 1, wherein the at least one bead has a size and configuration that prohibits the passage of the at least one bead from the bladder into a lumen of a ureter.

3. The ureteral stent of claim 1, wherein said proximal portion of said elongated body portion is substantially more compressible than the other portions of said elongated body portion.

4. The ureteral stent of claim 1, wherein the retention module includes a plurality of beads.

5. The ureteral stent of claim 1, wherein said at least one tether connector is substantially elastic.

6. The ureteral stent of claim 1, wherein said tether connector is substantially rigid.

7. The ureteral stent of claim 1, wherein said distal portion of said elongated body portion comprises a planar spiral loop for retention in the renal pelvis.

8. The ureteral stent of claim 1, wherein said elongated body portion is substantially rigid to prevent its deformation during insertion through the ureter.

9. The ureteral stent of claim 1, wherein said elongated body portion defines a plurality of openings along its length.

10. The ureteral stent of claim 1, wherein the at least one bead is substantially spherical.

11. The ureteral stent of claim 1, wherein said bead is substantially spherical, substantially oval, substantially tear-shaped, or substantially peanut-shaped.

12. The ureteral stent of claim 1, wherein said bead is made of a polymer.

13. A method of treating at least partial ureteral obstruction of a patient, comprising:
(a) providing a medical device comprising an elongated body portion defining a lumen, the body portion comprising a proximal end for placement in one of a ureter and a bladder of the patient, a distal end for placement in a kidney of the patient, a proximal portion, and a distal portion, the medical device further comprising a retention module disposed proximal to said proximal end of the elongated body portion, said retention module comprising at least one bead attached to the elongated body portion by at least one tether connector, the bead having a diameter between 3 and 10 millimeters, the bead being substantially buoyant relative to urine; and
(b) inserting the medical device into the patient such that the at least one bead is positioned in the bladder of the patient.

14. The method of claim 13, wherein the at least one bead has a size and configuration that prohibits the passage of the bead from the bladder into a lumen of a ureter.

15. The method of claim 13, wherein the retention module has a plurality of beads.

16. The method of claim 13, wherein said at least one tether connector is substantially elastic.

17. The method of claim 13 wherein said tether connector is substantially rigid.

18. The method of claim 13 wherein said distal portion comprises a planar spiral loop for retention in the renal pelvis.

19. The method of claim 13, wherein said elongated body portion is substantially rigid to prevent its deformation during insertion through the ureter.

20. The method of claim 13, wherein said elongated body portion defines a plurality of openings along its length.

21. The method of claim 13, wherein the bead is substantially spherical.

22. The method of claim 21, wherein the diameter of the bead is greater than the diameter of a lumen of a ureter.

23. The method of claim 13, wherein said bead is substantially spherical, substantially oval, substantially tear-shaped, or substantially peanut-shaped.

24. The method of claim 13, wherein said bead is made of a polymer.

25. A medical device for use within a body cavity, the medical device comprising:
   an elongated body portion defining a lumen, said elongated body portion comprising a proximal end for placement within one of a ureter and a bladder of a patient, a distal end for placement within a kidney of the patient, a proximal portion and a distal portion and said elongated body portion including a plurality of pores, said distal portion comprising a planar spiral; and
   a plurality of retention modules, at least one of said plurality of retention modules being attached to said proximal end of said elongated body portion, said at least one of said plurality of retention modules comprising at least one substantially spherical bead attached to the proximal end of said elongated body portion by a substantially elastic tether connector, said bead having a diameter between 3 and 10 millimeters and being substantially buoyant relative to urine.

26. A ureteral stent for placement in a ureter comprising:
   an elongated body portion defining a lumen, the body portion comprising a proximal end, a distal end, a proximal portion, and a distal portion, the proximal portion of the elongated body portion is substantially more compressible than the other portions of the elongated body portion; and
   a retention module disposed proximal to the proximal end of the elongated body portion, the retention module having a first fixation element attached to the elongated body portion by a tether connector, the retention module having a second fixation element attached to the elongated body portion.

27. The ureteral stent of claim 26, wherein the retention module has a size and configuration that prohibits the passage of the fixation element from a bladder of a patient into a lumen of a ureter of the patient.

28. A ureteral stent for placement in a ureter comprising:
   an elongated body portion defining a lumen, the body portion comprising a proximal end, a distal end, a proximal portion, and a distal portion, the proximal portion of the elongated body portion is substantially more compressible than the other portions of the elongated body portion; and
   a retention module disposed proximal to the proximal end of the elongated body portion, the retention module having a first fixation element and a second fixation element attached to the elongated body portion by a tether connector.

29. The ureteral stent of claim 26, wherein the first fixation element includes a substantially spiral configuration.

30. A ureteral stent for placement in a ureter comprising:
   an elongated body portion defining a lumen, the body portion having a proximal end and a distal end; and
   a retention module disposed proximal to the proximal end of the elongated body portion, the retention module having a first fixation element attached to the elongated body portion by a tether connector, the first fixation element having a substantially spiral configuration, the retention module having a second fixation element attached to the elongated body portion.

* * * * *